United States Patent [19]
Crowther et al.

[11] Patent Number: 5,504,049
[45] Date of Patent: Apr. 2, 1996

[54] TRANSITION METAL OLEFIN POLYMERIZATION CATALYSTS

[75] Inventors: Donna J. Crowther, Baytown; Richard A. Fisher, League City; Jo Ann M. Canich, Webster; Gregory G. Hlatky; Howard W. Turner, both of Houston, all of Tex.

[73] Assignee: Exxon Chemical Patents Inc., Wilmington, Del.

[21] Appl. No.: 86,772

[22] Filed: Jul. 1, 1993

Related U.S. Application Data

[63] Continuation-in-part of Ser. No. 907,098, Jul. 1, 1992, abandoned.

[51] Int. Cl.$^6$ .................. C08F 4/69; C08F 4/68
[52] U.S. Cl. .......... 502/117; 502/103; 502/104; 502/152; 502/155; 556/7; 556/12; 556/43; 556/57; 526/127; 526/133; 526/134; 526/129
[58] Field of Search .................. 502/117, 103, 502/152, 155, 104; 556/7, 12, 43, 57

[56] References Cited

U.S. PATENT DOCUMENTS

| | | | |
|---|---|---|---|
| 4,530,914 | 7/1985 | Ewen et al. | 502/113 |
| 4,701,432 | 10/1987 | Welborn, Jr. | 502/113 |
| 4,892,851 | 1/1990 | Ewen et al. | 502/104 |
| 5,006,500 | 4/1991 | Chang | 502/107 |
| 5,008,228 | 4/1991 | Chang | 502/111 |
| 5,017,714 | 5/1991 | Welborn, Jr. | 556/12 |
| 5,036,034 | 7/1991 | Ewen | 502/117 |
| 5,155,080 | 10/1992 | Elder et al. | 502/152 |
| 5,162,466 | 11/1992 | Karol et al. | 526/132 |
| 5,194,534 | 3/1993 | Bell | 526/161 |
| 5,198,401 | 3/1993 | Turner et al. | 502/155 |
| 5,320,996 | 6/1994 | Carney et al. | 502/113 |

FOREIGN PATENT DOCUMENTS

| | | |
|---|---|---|
| 0277003 | 8/1988 | European Pat. Off. . |
| 0277004 | 8/1988 | European Pat. Off. . |
| 0418044 | 3/1991 | European Pat. Off. . |
| 0427697 | 5/1991 | European Pat. Off. . |
| 0495375 | 7/1992 | European Pat. Off. . |
| 0509294 | 10/1992 | European Pat. Off. . |
| 0520732 | 12/1992 | European Pat. Off. . |
| 0532098 | 3/1993 | European Pat. Off. . |
| WO91/09882 | 7/1991 | WIPO . |
| WO92/00333 | 1/1992 | WIPO . |

OTHER PUBLICATIONS

Thomas et al., "Paramagnetic Alkylchromium Compounds as Homogenous Catalysts for the Polymerization", 1991, pp. 893–902, *J. Am. Chem. Soc.,* vol. 113.

Herberich, G. E., Comprehensive Organometallic Chemistry, The Synthesis, Reactions and Structures of Organometallic Compounds, vol. 1, pp. 381–410, Pergamon Press, Oxford.

Schmidt, Gregory F., and Maurice Brookhart, Implications of Three–Center, Two–Election M–H–C Bonding for Related Alkyl Migration Reactions: Design and Study of an Ethylene Polymerization Catalyst, J. Am. Chem. Soc. 1985, 107, pp. 1443–1444.

Devore et al., Complexes of (Arylimido)vanadium(V). Synthetic, Structural, Spectroscopic, and Theoretical Studies of V(Ntol)Cl$_3$ and Derivatives, J. Am. Chem. Soc. 1987, 109, pp. 7408–7416.

Ballard et al., Alkyl Bridged Complexes of the Group 3A and Lanthanoid Metals as Homogenous Ethylene Polymerisation Catalysts, Journal of The Chemical Society, Chemical Communications, 22, 1978, pp. 994–995.

Shapiro et al., Unique Example of a Single–Component–Olefin Polymerization, Organometallics 1990, 9, pp. 867–869.

*Primary Examiner*—Mark Nagumo
*Attorney, Agent, or Firm*—F. E. Reid; M. S. Spiering

[57] ABSTRACT

This invention relates to non-Group 4 transition metal compositions useful as olefin polymerization catalysts, wherein the transition metal is in a high oxidation state. The invention further relates to design of new ligand systems and methods of preparing and using the same. Compositions useful as catalyst precursors are neutral transition metal complexes comprising the unique ligand systems of the invention. The inventive compositions may be activated to a catalytic state by ion-exchange reagents or by Lewis acids.

30 Claims, No Drawings

TRANSITION METAL OLEFIN POLYMERIZATION CATALYSTS

CROSS REFERENCE TO RELATED APPLICATIONS

This application is a continuation-in-part to U.S. Ser. No. 907,098, filed on Jul. 1, 1992, now abandoned.

FIELD OF THE INVENTION

This invention relates to transition metal polymerization catalyst systems from Groups 5–10, wherein the active transition metal center is in a high oxidation state and stabilized by low coordination number polyanionic ancillary ligand systems, the use thereof, and to the method of preparing and using the same.

BACKGROUND OF THE INVENTION

Traditional Ziegler-Natta type catalysts for the polymerization of olefins have been known since the 1950's. Generally, these catalysts comprise a transition metal halide compound, particularly one of titanium and chloride, and a metal alkyl cocatalyst, particularly an aluminum alkyl cocatalyst. The traditional catalyst systems are generally comprised of several chemically distinct active metal sites which produce different polymeric materials (molecular weight comonomer, etc.) under steady state reactor conditions. During the last 30 years of development, traditional Ziegler-Natta catalysts have been optimized and provide low cost routes to a variety of commercially important polyolefins, however further improvements over the control of key polymer structure parameters such as molecular weight distribution (MWD), composition distribution (CD), end group functionality, sequence distribution and polar comonomer compatibility are still needed.

Recent progress to improve the Ziegler-Natta system has been directed towards the production of soluble, single sited olefin polymerization catalysts derived from transition metal precursors where the halide ligands used in tradition catalysts have been replaced by bulky, organic ancillary ligand systems, such as cyclopentadienyl (Cp) derivatives. In contrast to simple halide ligands, the bulky ancillary ligand systems are not susceptable to removal or change during polymerization, stabilize a single form of the catalyst, and can be modified in a rational way to change the properties of the catalyst center. The development of high activity catalyst systems derived from bis- and mono- Cp stabilized Group 4 metal precursors and alumoxanes is now well documented. Despite the fact that the cocatalyst (and therefore the resulting catalyst) is a chemically complex mixture of aluminum alkyl reagents, the active catalyst generally behaves as a single sited catalyst and produces narrow MWD polyolefins.

Recent advances in the art have led to the development of well defined (discrete), ancillary ligand stabilized single-sited olefin polymerization catalysts of the Group 3 and 4 transition metals. These systems do not rely on the use of alkyl aluminum cocatalysts, and offer improvements in terms of cost and product versatility. Examples of mono-Cp and bis Cp based Group 3 and 4 discrete catalysts are represented below.

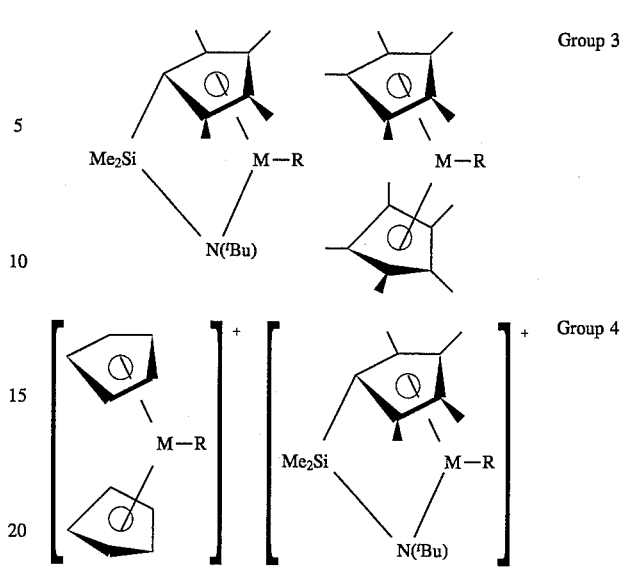

The neutral Group 3 systems were prepared and studied by Ballard et al. (J. Chem. Soc., Chem. Comm., (1978) p. 994–995) and Bercaw et at. (Organometallics, Vol. 9 (1990) pp. 867–869). The work of Bercaw and others in this field has demonstrated that the neutral, three-coordinate systems tend to dimerize to form inactive four-coordinate systems when the size of the ancillary ligands is decreased. The use of bulky Cp ligands to sterically prevent self-dimerization and maintain catalytic activity has been successful, but the resulting systems are often too sterically hindered to allow for the incorporation of larger olefin monomers.

The discovery of isostructural and isoelectronic discrete mono- and bis-Cp based Group 4 cationic systems, are discussed in European Patent Application (EPA) 277,003 and EPA 277,004, PCT International Application WO 92/00333 and EPA 418,044. These cationic systems are stabilized by the ancillary ligand system and are isolated as the salts of specially designed compatible non-coordinating artions. The development of compatible non-coordinating anions, as disclosed in EPA 277,003 and 277,004 represents a major advance in the field because they provide a means by which highly reactive coordinatively unsaturated organometallic cations can be generated and isolated. Although the ionic Group 4 catalysts are greatly improved over the organoaluminum activated systems in terms of producing polymers having greater molecular weight, enhanced molecular weight distribution and composition distribution control, there exists a need to provide a catalyst with improved thermal stability, product versatility, and tolerance to polar functionality.

The need for improved single sited olefin polymerization catalysts is evident, particularly in terms of chemical stability (e.g., air stability) and tolerance to polar functionality. Improvements in these properties would yield catalysts which could tolerate greater levels of impurities in the monomer feeds, and which could incorporate polar comonomers into a polyolefin backbone. For this reason, it would be desirable to develop olefin polymerization catalyst comprised of later transition metals. The best studied and well defined late metal catalysts for the polymerization of ethylene has been developed by Brookhart and coworkers (J. Am. Chem. Soc. 1985, 107, 1443–1444). These systems, $Cp^*Co(L)R^+BX_4^-$, are comprised of cationic cobalt (III) complexes containing a ligand, $Cp^*$, a neutral datively bound ligand, L, and a reactive sigma-bound alkyl with the charge on the metal center balanced by a borate anion $BX_{4-}$.

While these catalyst systems offer some potential advantages, particularly with respect to compatibility with polar functionalities and for the production of very narrow molecular weight distributions, they suffer from very low activity and yield only a single polymer chain per metal atom. A goal is to develop polymerization catalysts which combine the activity and yield of cationic Group 4 systems with the selectivity and functional group tolerance of later metal systems.

SUMMARY OF THE INVENTION

This invention relates to Group 5–10 transition metal polymerization catalysts, wherein the transition metal is in a high oxidation state, stabilized by a low coordination number ancillary ligand system(s), the use thereof, and to methods of preparing and using the same. The catalyst is an ion-pair comprised of a coordinatively unsaturated cationic transition metal complex having at least one reactive metal-ligand sigma bond and stabilized by a low coordination number polyanionic ancillary ligand system and charge balanced by compatible non-coordinating anions. The catalyst precursor, a neutral low coordination number ancillary ligand containing transition metal complex, can be converted into the active ionic catalyst using Lewis acid activators such as methylalumoxane or $B(C_6F_5)_3$, or by ion-exchange reagents comprising a reactive cation and a compatible non-coordinating anion. The invention more particularly relates to compositions useful as olefin polymerization catalysts for the production of polyolefins containing from 2 to 20 carbon atoms.

The preferred catalyst of this invention are ion-pairs comprising a cationic Group 5 or 6 transition metal complex defined by the following formula:

$$([\{(L_3)A(L_4)\}^{-c}M_n(X)]^{+1})_q['B^{-m}]_p$$

wherein:

M is a Group 5 or 6 transition metal in its highest formal oxidation state;

n is the Group number of the metal;

$L_3$ and $L_4$ are the same or different substituted or unsubstituted bulky anionic ancillary ligands covalently bonded to the metal;

A is an optional bridging group linking $L_3$ and $L_4$;

c represents the negative charge on the ancillary ligand system $\{L_3AL_4\}$;

c+2=n.

X is a uninegative ligand selected from hydride radicals, hydrocarbyl radicals, halogen-substituted hydrocarbyl radicals, halocarbyl radicals, hydrocarbyl-substituted organometalloid radicals, halocarbyl-substituted organometalloid radicals;

'B is a compatible non-coordinating anion of charge –m;

p is the number of 'B anions;

q is the number of +1 cations;

p times m=q $$[\{(L_3)A(L_4)\}^{-c}M_n(X)]_q^{+1}['B^{-m}]_p$$

'B is preferably a single anionic coordination complex comprising a plurality of lipophilic radicals covalently coordinated to and shielding a central charge-bearing metal or metalloid atom, which anion is bulky, labile and capable of stabilizing the transition metal compound.

'B may be represented by the formula:

$$M[Q_1Q_2..O_n]^{-d}$$

wherein:

M is a metal or metalloid;

$Q_1$ to $Q_n$ are, independently, hydride radicals, bridged or unbridged dialkylamido radicals, alkoxide and aryloxide radicals, hydrocarbyl and substituted hydrocarbyl radicals, halocarbyl and substituted halocarbyl radicals, and hydrocarbyl- and halocarbyl-substituted organometalloid radicals and any one, but not more than one of $Q_1$ to $Q_n$ may be a halide radical;

n is the total number of Q ligands; and d is an integer representing the total charge on the anion.

$$\{(L_3)A(L_4)\}^{-c}M_nX_2$$

wherein:

M is a Group 5 or 6 transition metal in its highest oxidation state (dO);

$L_3$ and $L_4$ are bulky, ancillary anionic ligands such that the sum of their formal anionic charge is equal to c;

c+2=n;

X is independently a uninegative ligand selected from hydride radicals, hydrocarbyl radicals, halogen-substituted hydrocarbyl radicals, halocarbyl radicals, hydrocarbyl-substituted organometalloid radicals, halocarbyl-substituted organometalloid radicals;

A is an optional bridging group linking $L_3$ and $L_4$; and, n is the group number of the metal;

with a second component comprising an ion-exchange compound comprising a cation, which will irreversibly react with at least one ligand, X, contained in said Group 5 or 6 metal compound and a compatible non-coordinating anion;

with an ionizing activator component which may be an ion-exchange compound comprising a cation, which will irreversibly react with at least one ligand, X, contained in said Group 5 or 6 metal compound and a noncoordinating anion. Alternatively, the transition metal compound may be reacted with a Lewis acid capable of abstracting the ligand X to form a compatible non-coordinating anion.

The compositions described may be placed on a support and optionally prepolymerized prior to use as a catalyst for olefin polymerization.

DETAILED DESCRIPTION OF THE INVENTION

Key features of known single-sited olefin polymerization catalysts include a coordinatively unsaturated, electrophilic metal center in a trigonal environment, an active sigma bound substituent, preferably an alkyl, and at least a single vacant orbital adjacent (cis) to the sigma bound ligand. A set of inert ancillary ligands are present in these systems to establish and maintain the proper electronic and steric environment of the metal center throughout the polymerization. Ancillary ligands may be defined as ligands which do not participate in the polymerization but which are covalently bonded to the metal by single or multiple bonds. Ancillary ligands are typically composed of organic and/or inorganic moieties in a discrete and well defined manner and preferably have a molecular weight about or greater than 50 amu (atomic mass unit). A prototypical example of an anicillary ligand is the Cp group. Neutral complexes containing the features of olefin polymerization catalysts defined above are unstable with respect to self dimerization unless very large ancillary ligands are present. Charged metal complexes meeting the above defined criteria of polymerization catalysts do not require bulky ancillary ligands to prevent self-dimerization. The use of electrostatic rather than steric forces to control dimedzation allows for much greater reactivity of these ionic species with larger olefinic substrates.

The electronic nature of the metal centers in these systems is critical in determining the ultimate reactivity of the catalyst. For early transition metal systems, complexes of the highest possible formal oxidation state ($d^0$ complexes) are preferred. In late metal systems such as Brookhart's cobalt complexes, the highest formal oxidation states are inaccessible. In these systems, the highest oxidation state which is accessible is desirable. Residual electron density at the metal center of these systems renders them more tolerant to polar functionality, but diminishes the rate of chain propagation relative to that of chain termination, and in some instances this results in low molecular weight polymers. The formation of high molecular weight polymer in these systems demands a careful balancing of the electron density at the metal center.

The challenge of capturing unique features of metal systems later than Group 4 lies in constructing higher oxidation state complexes which remain coordinatively unsaturated. This invention relates to the design and use of ligand systems based on low coordination number polyanionic ligands for the construction of olefin polymerization catalysts based transition metals of groups greater than Group 4. Low coordination-number polyanionic ancillary ligands (LCPALs) are defined as ancillary ligands which have a greater formal negative charge than the number of sites they occupy. As a system, these ligands possess the unique property of oxidizing the metal center to a greater extent than they fill occupation sites on that metal and thus provide a method of maintaining high oxidation states and low coordination numbers.

The single-sited olefin polymerization catalysts of this invention are comprised of a coordinatively unsaturated cationic transition metal complex from the Groups 5–10 of the Periodic Table having (Grant & Hackh's Chemical Dictionary 5th ed. 1987, p. 433) having at least one reactive metal—ligand sigma bond and stabilized by a low coordination number polyanionic ancillary ligand system. The ancillary ligand system is designed to stabilize the metal in a high oxidation state using a minimum number of coordination sites (preferably 2). Illustrative but not limiting examples of polyanionic ligands which can be used in this invention include bulky imides such as t-butylimido and 2,6-diisopropylimido, and carbolides such as $C_2B_9H_{11}^{-2}$ and $CB_{10}H_{11}^{-3}$. The polyanionic ligands can be used alone, or in combination with conventional monoanionic ancillary ligands (such as Cp derivatives, alkoxides, aryloxides, amides phosphides, and the like) or neutral ancillary ligands (such as phosphines, amines, carbonyls and the like) to form an ancillary ligand system. Two ancillary ligand systems may be optionally bridged together through a bridging group, A. In addition, the cationic transition metal complex may be stabilized by a displaceable Lewis base ligand. The cationic transition metal complex is charge balanced by compatible non-coordinating artions which are weakly coordinated to the active metal center thereby being sufficiently labile to be displaced by a neutral Lewis base such as an olefin. As recited herein the term "compatible non-coordinating anion" specifically refers to anions which are bulky relative to the size of the vacant coordination site and which are resistant to chemical reactions with the active metal center, such as transfer of a negatively charged fragment to the cation to form neutral biproducts. Illustrative but not limiting examples of cations of this invention include $d^0$ Group 5 systems such as $(C_5Me_5)(C_2B_9H_{11})TaCH_3^+$, wherein Me is methyl, and $(C_5Me_5)(RN)TaCH_3^+$ (where R=alkyl or aryl); $d^0$ Group 6 systems such as $(C_2B_9H_{11})_2WCH_3^+$ and $(RN)_2WMe^+$, $d^0$ Group 7 systems such as $(C_2B_9H_{11})(CB_{10}R_{11})ReMe^+$, $d^0$ Group 8 systems such as $(CB_{10}H_{11})_2OsMe^+$, and $d^6$ Group 10 systems such as $(C_2B_9H_{11})(Ph_3P)NiCH_3^+$ where Ph is phenyl, and Lewis base adducts thereof.

The active catalysts of this invention can be prepared from a neutral transition metal precursor comprising the polyanionic ligand system using a variety of activating strategies. One general strategy for forming the active catalyst involves reacting the neutral precursor with an ion-exchange compound comprising a cation capable of removing a negatively charged ligand (or electron) from the neutral transition metal precursor and a compatible non-coordinating anion. Another approach involves the use of discrete Lewis acid coactivators such as $B(C_6F_5)_3$ with the neutral transition metal precursor to remove an anionic non-ancillary ligand from the transition metal precursor to form the active catalyst eation and a non-coordinating anion comprised of the Lewis acid coordinated to the artionic non-ancillary ligand. In general, active catalysts can also be generated using alumoxanes, preferrably methylalumoxane in combination with the neutral transition metal precursor. A more detailed description of these approaches is given below.

PREFERRED EMBODIMENTS

The preferred catalysts of this invention are Group 5 and 6 transition metal catalysts having the following general structural features: 1) two ancillary stabilizing ligands; 2) one reactive sigma metal-ligand bond such as a metal carbon or hydride bond; 3) the metal center in its highest formal oxidation state ($d^0$); and 4) a total formal charge of +1 on the transition-metal center. The prefered catalysts comprise the ion pair represented by the formula:

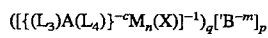

wherein:

M is group 5 or 6 transition metal in its highest oxidation state;

n is the group number of the metal;

$L_3$ and $L_4$ are the same or different substituted or unsubstituted anionic ancillary ligands covalently bonded to the metal;

X is a uninegative ligand selected from hydride radicals, hydrocarbyl radicals, halogen-substituted hydrocarbyl radicals, halocarbyl radicals, hydrocarbyl-substituted organometalloid radicals;

A is an optional bridging group bridging $L_3$ and $L_4$;

c is an integer representing the charge on the ancillary ligand system $\{(L_3)A(L_4)\}$;

c+2=n

'B is a compatible non-coordinating anion of charge –m;

p is the number of B anions;

q is the number of +1 cations; and p times m =q.

The optional X-ligands given in the above formula are the preferred selections. Other X-ligand options are also suitable for catalysts of this invention, for example, any X-group which forms a single metal-ligand sigma bonds with little or no pi or multiple bond character. Thus, metal complexes containing metal X-ligands other than those listed in the formula above that are bonded to the metal through a single sigma bond with no multiple bond character are operable and included in this invention.

The ancillary ligand system comprised of $\{L_3—A—L_4\}$ is a low coordination number polyanionic ligand system for which the total anionic charge of $\{L_3—A—L_4\}$ is greater than the number of coordination sites it occupies. Those of ordinary skill in the art will recognize that for unbridged ancillary ligands, Group 5 catalysts will be comprised of one dianionic LCPAL, one uninegative ancillary ligand, and one uninegative ligand X, defined above. Similarly, Group 6 metal catalysts will be comprised of two dianionic LCPALs and one uninegative ligand X, or one trianionic LCPAL, one uninegative ancillary ligand, and one uninegative ligand X. The bridging of ligands $L_3$ and $L_4$ with neutral, non-coordinating, bridging groups A results in the formation of a single ligand for which the charge and coordination number are the sum of those for $L_3$ and $L_4$. The use of anionic, non-coordinating, bridging groups A allows for the construction of LCPALs from uninegative ancillary ligands which are well known in the art. The ancillary ligand system $\{(L_3)A(L_4)\}$ has a weight average molecular weight of about or greater than 100 grams/mole.

Illustrative but not limiting examples of ancillary ligands from which to chose a ligand set meeting the above criteria include: uninegative ancillary ligands well known to those of skill in the art such as substituted or unsubstituted Cp moieties, amides such as bis-trimethylsilylamido, bis-t-butylamides, bulky alkoxides such as tri-t-butylalkoxide; dianionic LCPALs such as oxo (=O), sulfido (=S), imido (=NR), phosphido (=PR), alkylidenes (=CR$_2$), cyclooctratetraenyl ($[C_8H_{8-x}R_x]^{-2}$), porphyrins, phthalocyanines, corrins, and other anionic polyazamacrocycles; carbollides (e.g. $[C_2B_9H_{11}]^{-2}$), bis(o-hydroxyphenyl)alkyl and -arylphosphine oxidos (h$^3$-(RPO(C$_6$H$_4$O)$_2$)$^{-2}$); and borollides; and trianionic LCPALs such as nitrido ligand (≡N), alkylidynes (≡CR), trianionic carbollides (e.g. $[CB_{10}H_{11}]^{-3}$) and trianionic corroles. Examples of LCPALs comprised of anionic bridging groups include $[Cp-B(Ph)_2-Cp']^{-3}$ where Cp and Cp' are substituted or unsubstituted cyclopentadienyl ligands. Higher valent LCPALs are known to bond to transition metals and can be used in this invention. The ancillary ligands and optional bridging groups on the first components of this invention may be substituted with a wide range of substituent types without rendering them inoperative as catalyst precursors. For example, all of the suitable substituents for catalyst precursors in the patent applications incorporated herein by reference may be used to modify the ancillary ligands and bridging groups of the first components and catalysts of this invention. These substituents may further be modified with any functionality which is not itself a catalyst poison. Furthermore, the size, as measured by molecular weight, of the substituent may be varied over a wide range without effecting the operability of the precursor or catalyst and thus are included in this invention.

The borollide ligands are illustrated in general formula:

$$(C_4R_xH_{4-x}BR')^{-2} \qquad 2.$$

wherein:

B is boron;

C is carbon;

each R and R' is, independently, a hydrocarbyl radical, substituted-hydrocarbyl radical, halocarbyl radical, substituted-halocarbyl radical, hydrocarbyl-substituted organometalloid radical, halocarbyl-substituted organometalloid radical, disubstituted Group 15 radical, substituted Group 16, or halogen radical; any two adjacent R groups or adjacent R and R' groups can be joined to form a cyclic substituent; and x is 0, 1,2,3, or 4.

Known methods of preparing borollide dianions, such as disclosed by G. E. Herberich, *Comprehensive Organometallic Chemistry* Pergamon Oxford, Vol. 1, p. 381–410 (1984), include the reduction of neutral borole precursors by alkali metals or their amalgams, reduction of neutral borole precursors within the coordination sphere of the low-valent transition metal complex, and deprotonation of 1-(dialkylamino)-2,5-dihydroboroles.

Illustrative, but not limiting, examples of suitable bridging groups A include: $C_1$-$C_n$ saturated or unsaturated hydrocarbyl diradicals, substituted or unsubstituted carbenoids $R_2C$, hydrocarbyl substituted silyl, germyl, or stanyl groups; and dialkyl and diaryl borates.

Examples of compatible non-coordinating anions include but are not limited to boranes, polynuclear boranes, carboranes, metallacarboranes, polyoxoanions, and anionic coordination complexes are well described in the literature (see EPA 277,003, EPA 277,004, EPA 520732 which are herein incorporated by reference). US Pat. No. 5,198,401 incorporated by reference herein, describes compatible non-coordinating anions, and artionic coordination complexes, and teaches to design superior counter anions. Preferred non-coordinating anions comprise a plurality of lipophilic radicals covalently coordinated to and shielding a central charge-beating metal or metalloid atom, which anion is bulky, labile and capable of stabilizing the transition metal cation. Anionic coordination complexes may be represented by the following formula:

$$M[Q_1Q_2..Q_n]^{-d} \qquad 3.$$

wherein:

M is a metal or metalloid;

$Q_1$ to $Q_n$ are, independently, hydride radicals, bridged or unbridged dialkylamido radicals, alkoxide and aryloxide radicals, hydrocarbyl and substituted hydrocarbyl radicals, halocarbyl and substituted halocarbyl radicals, and hydrocarbyl- and halocarbyl-substituted organometalloid radicals and any one, but not more than one of $Q_1$ to $Q_n$ may be a halide radical;

n is the total number of Q ligands; and d is an integer representing the total charge on the anion. The most preferred compatible non-coordinating anions comprise at least three perfluorophenyl groups coordinated to boron and are represented by the formula $B(pfp)_3Q_{-1}$ (where pfp =$C_6F_5$).

The catalyst composition defined in equation (1) can react with Lewis base ligands which may be present as by-products of the first component synthesis or which may be added in catalyst to form coordination complexes of (1). The resulting coordination complex will generally be an active catalyst for olefin polymerization, however, the activity and or performance of the catalyst may be modified by the choice of Lewis base.

The Group 5 or 6 transition metal catalyst described may be employed in solution, slurry, bulk-phase, high pressure or gas-phase polymerization processes, or a combination thereof, to produce a polyolefin of high molecular weight, high comonomer content, and/or narrow molecular weight distribution.

Catalyst Preparation

The catalysts are preferably prepared by combining at least two components, the Group 5 or 6 transition-metal-containing component (first component) containing at least one ligand capable of reacting with a second, ionizing activator component (second component). The transition-metal component, or catalyst precursor, is comprised of the first component represented by the following formula:

$$\{(L_3)A(L_4)\}^{-c}M_nX_2 \qquad 4.$$

wherein:

M is a Group 5 or 6 transition metal in its highest oxidation state (dO);

$L_3$ and $L_4$ are bulky, ancillary anionic ligands such that the sum of their formal anionic charge is equal to c;

c+2=n;

X is independently a uninegative ligand selected from hydride radicals, hydrocarbyl radicals, halogen-substituted hydrocarbyl radicals, halocarbyl radicals, hydrocarbyl-substituted organometalloid radicals, halocarbylsubstituted organometalloid radicals;

A is an optional bridging group linking $L_3$ and $L_4$; and, n is the group number of the metal;

with a second component comprising an ion-exchange compound comprising a cation, which will irreversibly react with at least one ligand, X, contained in said Group 5 or 6 metal compound and a compatible non-coordinating anion.

The preparation of first components having the structure defined in equation 4 depends upon the choice of $L_3$ and $L_4$. In general, synthetic stategies for preparing transition metal complexes comprising the mono- and poly-valent ancillary ligands of this invention are known in the art and can be applied to the synthesis of the desired first component. In a typical preparation the lithium salts of $L_3$, $L_4$, or $L_3AL_4$ are combined in an organic solvent with the metal halide in its highest oxidation state. Other conventional salts such as Group 1 salts or Grignards of Group 2 salts may be employed. In some cases, such as when imide is used, the lithium salt approach may not be ideal and standard "imide" transfer reactions can be used. Generally the ancillary ligands of this invention may be prepared in accordance with known procedures.

Second components useful for converting the transition metal precursor (4) into the catalytically active ion-pair (1) are either an ion exchange reagent as defined in equation (5) or a well defined Lewis acid defined in equation (6) below:

$$M[Q_1Q_2..Q_n]^{-d} \qquad 5.$$

wherein:

M is a metal or metalloid;

$Q_1$ to $Q_n$ are, independently, hydride radicals, bridged or unbridged dialkylamido radicals, alkoxide and aryloxide radicals, hydrocarbyl and substituted hydrocarbyl radicals, halocarbyl and substituted halocarbyl radicals, and hydrocarbyl- and halocarbyl-substituted organometalloid radicals and any one, but not more than one of $Q_1$ to $Q_n$ may be a halide radical;

n is the total number of Q ligands; and d is an integer representing the total charge on the anion.

$$M'(Q)_r \qquad 6.$$

wherein:

M' is a metal or metalloid in its highest oxidation state;

r represents the number of Q ligands;

and Q is selected from the group consisting of hydride radicals, dialkyamido radicals, alkoxide and alkoxide radicals, hydrocarbyl and substituted hydrocarbyl radicals, halocarbyl and substituted halocarbyl radicals, and hydrocarbyl- and halocaryl-substituted organometalloid radicals. M' is preferably boron and Q is preferably $C_6F_5$.

Upon combination of the first and second components, the second component, or at least a portion thereof, reacts with one of the ligands of the first component, thereby generating an ion pair consisting of a transition-metal cation and the aforementioned anion, 'B, which anion is compatible with the transition-metal cation formed from the first component. The anion must generally be capable of stabilizing the transition-metal cations ability to function as a catalyst and must generally be non-coordinating or sufficiently labile to permit displacement by an olefin, diolefin, or acetylenically unsaturated monomer during polymerization.

Catalyst precursors represented by equation 4 may be converted to the active catalysts represented in equation 1 by several routes depending on the nature of the precursors and ligands X. A list of illustrative, but not limiting examples of such methods are disclosed below.

The first method involves contacting the first component (4) with a second component $[Ct]_m['B]^{m-}$ where the cation Ct is an oxidizing agent which is reduced during the formation of the ion pair of equation 1. Examples of preferred second components for this application include $[Cp'_2Fe]+['B]^-$ and $Ag^+['B]^-$ (where 'B is $B(pfp)_3Q_1$ as defined above). For less reactive first components more highly oxidating cations may be employed. This approach is useful with first components with low oxidation potentials.

A second method uses Bronsted acid salts of compatible non-coordinating anions as the second component having the following general formula:

$$[LH]^{+m}['B^{-m}] \qquad 7.$$

wherein:

[LH] is a Bronsted Acid of charge +1

L is a neutral Lewis base;

'B is a compatible non-coordinating artion; and m represents the charge of 'B and the number of [LH] cations.

When the two components are combined in a suitable solvent (aliphatic or aromatic solvents are preferred) the acidic proton of the cation reacts with one of the X-ligands of the first component to liberate a non-reactive neutral product (X-H), a neutral Lewis base L, which may remain in solution or weakly bind to the metal cation, and the composition defined by equation 1. This approach is generally useful for first components having X-ligands which are hydrolyzable by water. Bronsted acid salts having acidic protons are preferred for first components which are resistant to degradation by water. Examples of Bronsted acid cations useful as cations of the second component include ammonium ions ($R_3NH^+$), phosphonium ions ($R_3PH^+$), and oxonium ions ($R_2OH^+$).

A third method involves reacting Lewis acid salts of compatible non-coordinating anions catalyst precursors with the first components of equation 4. Examples of Lewis acidic cations useful as cations of the second component include reactive transition metal cations such as $[Cp_2MMe(NR_3)]^+$ (where M=a Group 4 metal), reactive carbonium ions such as $[CPh_3]^+$ and tropylium, and organometallic main group cations such as $[ZnMe]^+$.

A fourth approach involves reacting well defined neutral Lewis acid second components with first components defined by equation 4. The neutral Lewis acid second components are generally defined by equation 6. The preferred Lewis acid is $B(pfp)_3$. The neutral Lewis acid removes a negatively charged X-ligand from the first component to form the active transition metal cation and the compatible non-coordinating anion (e.g. when $B(pfp)_3$ is used the non-coordinating anion is $B(pfp)_3X\_$). In general, increasing the Lewis acidity of the second component by introducing electron withdrawing groups on the ligand system will lead to more powerful coactivators capable of activating a wider variety of first components.

Other approaches for the production of catalysts of this invention which do not rely on the first component defined by equation 4 include the two general procedures listed below.

The first method involves reacting a second component comprising an oxidizing cation with the first component defined below:

$$\{(L_3)A(L_4)\}^{-c}M_nX \qquad 8.$$

wherein the symbols are defined in equation 4 except there is only one X-ligand and the metal is in the n−1 oxidation state ($d^1$). Examples of preferred second components for this application include $[Cp'_2Fe]+['B]^-$, $Ag^+['B]^-$ (where 'B is $B(pfp)_3Q_1$ as defined above).

Another general method involves adding one or more of the stabilizing ancillary ligands to the metal center subsequent to the formation of the cationic center. For example, the reaction of equimolar amounts of $C_2B_9H_{13}$ and $[Cp*TaMe3]^+['B\ ]^-$ could lead to the formation of $[Cp*(C_2B_9H_{11})TaMe]^+['B]^-$ wherein Cp* can be a substituted or unsubstituted Cp group.

Yet another general method of activating the first components of equation 4 involves the use of hydrolyzed Lewis acids defined by the following general formulae:

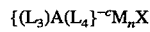
$$(R^3—Al—O)_s \qquad 9.$$

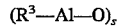
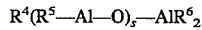
$$R^4(R^5—Al—O)_s—AlR^6_2 \qquad 10.$$

It will be apparent to those of skill in the art that a wider variety of X groups on the first component may be used when alumoxanes are the cocatalyst. These include halides, alkoxides, amides, phosphides and the like.

In the general formulae 9 and 10, representing alumoxane or a derivate thereof, Al is aluminum, 0 is oxygen, $R^3$, $R^4$, $R^5$ and $R^6$ are, independently a $C_1$–$C_6$ alkyl radical, for example, methyl, ethyl, propyl, butyl or pentyl and "s" is an integer from 1 to 50. Most preferably, $R^3$, $R^4$, $R^5$ and $R^6$ are, each methyl and "s" is at least 4. When an alkyl aluminum halide is employed in the preparation of the alumoxane, one or more $R^{3-6}$ groups may be halide.

As is now well known, alumoxanes can be prepared by various procedures. For example, a trialkyl aluminum may be reacted with water, in the form of a moist inert organic solvent; or the trialkyl aluminum may be contacted with a hydrated salt, such as hydrated copper sulfate suspended in an inert organic solvent, to yield an alumoxane.

Suitable alumoxanes which may be used in the catalysts of this invention are those prepared by the hydrolysis of a trialkylaluminum, such as trimethylaluminum, triethylaluminum, tripropylaluminum, triisobutylaluminum, dimethylaluminum chloride, diisobutylaluminum chloride, diethylaluminum chloride. The most preferred alumoxane for use is methylalumoxane (MAO). Methylalumoxanes having an average degree of oligomerization of from 4 to 25 ("s"=4 to 25), with a range of 13 to 25 are the most preferred and employed in a mole ratio of MAO to transition-metal component of 1:1 to $10^6$:1.

In general, the catalyst of this invention can be prepared by combining the first and second components in a suitable solvent or diluent at a temperature within the range of −100° C. to 300° C. The catalyst may be used to polymerize olefins, including cyclic olefins, alpha-olefins, diolefins, and/or acetylenically-unsaturated monomers having 2 or more carbons atoms, either alone or in combination with other monomers or monomer mixtures. In general, the polymerization can be accomplished at conditions known in the art. It will, of course be appreciated that the catalyst will form in situ if the components thereof are added directly to the polymerization process and a suitable solvent or diluent, including condensed monomer, is used in said polymerization process. It is, however, preferred to form the catalyst in a separate step in a suitable solvent or diluent prior to adding the same to the polymerization step. Preferred temperatures for the reaction of the two components are from −30° C. to 100° C., with holding times from 15 seconds to 60 minutes. The catalyst may contain pyrophoric species, especially methylalumoxane, and should be handled and transferred in an inert atmosphere such as nitrogen, argon, or helium.

As indicated above, the improved catalyst of this invention will, preferably, be prepared in a suitable solvent or diluent. Suitable solvents or diluents include any of the solvents known in the prior art to be useful in the polymerization of monomers. Suitable solvents, then, include, but are not limited to, straight- and branched-chain aliphatic hydrocarbons such as isobutane, butane, hexane, heptane, octane; cyclic and alicyclic aliphatic hydrocarbons such as cyclohexane, cycloheptane, methylcyclohexane; and aromatic and alkyl-substituted aromatic solvents such as benzene, toluene, and xylene. Suitable solvents also include liquid olefins which may act as monomers or comonomers including ethylene, propylene, butadiene, cyclopentene, 1-hexene, 3-methyl-1-pentene, 1,4-hexadiene.

In order to achieve greater control of polymer particle size and distribution and compatibility with gas-phase polymerization processes, the catalysts may be supported on appropriate inert materials, as described in U.S. Pat. Nos. 4,701,432, 5,006,500, 5,008,228, and as described in PCT International Application WO 91/09882. The supported catalysts may be optionally prepolymedzed with olefinic monomers.

Having thus broadly described the present invention and preferred embodiments thereof, it is believed that the same will become even more apparent by reference to the following examples. It will be appreciated, however, that the examples are presented solely for the purpose of illustration and should not be construed as limiting the invention. All the examples were carded out in dry, oxygen-free atmospheres and solvents, molecular weights are reported as weight average molecular weights, MAO was purchased from Schering Company, Dublin Ohio.

EXAMPLE 1

First Component Synthesis

In an inert atmosphere, vanadium oxide trichloride (2.75 g) was dissolved in dichloromethane (100 ml) and potassium tris(pyrazolyl)borate (2.0 g) added slowly. The mixture, which turned from dark orange to purple, was stirred overnight. The volatiles were removed in vacuo. A 70:30 pentane/dichloromethane mixture was added and the solids were collected, washed with pentane until no color was observed in the washings, and dried. Yield: 3.28 g. The 1H NMR spectrum ($CD_2Cl_2$) of the solid showed this to be a diamagnetic solid, tris(pyrazolyl)borato vanadium oxide dichloride. A 1 gram sample was dissolved in boiling toluene (60 ml), filtered, and the tiltrate reduced in vacuo. Crystallization from dichloromethane-pentane yielded 0.45 g of product.

Ethylene Polymerization

To a 1 liter stainless-steel autoclave, previously purged with nitrogen, was added 5 ml of a 9.5 weight percent solution of methylalumoxane in toluene. 400 ml of dry, deoxygenated hexane were then added, followed by a solution of the catalyst of Example 1 (30 mg) in toluene (5 ml). The contents of the autoclave were stirred, heated to 60° C., and pressurized with ethylene (200 psi) (13.6 atm). After 30 minutes, the autoclave was cooled and vented. The polyethylene formed was isolated by filtration and dried. Yield: 16 g.

EXAMPLE 2

Ethylene Polymerization

Ethylene was polymerized in a manner similar to that of Example 1 using (cyclopentadienyl)vanadium (p-tolyimido) dichloride, prepared by the method reported by Maatta et at., (*Journal of the American Chemical Society*, Volume 109 (1987), pp. 7408–74 16) as the metal component. The yield of linear polyethylene was 5.8 g.

EXAMPLE 3

Catalysis Synthesis

Preparation of $Cp^*(C_2B_9H_{11})TaMe_2$ (where Me $=CH_3$, and $Cp^* =C_5Me_5$): $Cp^*TaMe4$ (1.0 g, 2.6 mmol, prepared by known literature procedures) and $C_2B_9H_{13}$ (0.36 g, 2.6 mmol, prepared by the known literature methods) were combined and stirred at room temperature in toluene for 30 minutes. The solvent was removed in vacuo to leave a solid yellow product. The crude product was extracted with toluene, filtered, concentrated to the point of crystallization. The yellow crystalline product was isolated by filtration and dried in vacuo to yield 0.4 grams of $Cp^*(C_2B_9H_{11})TaMe_2$ (as characterized by NMR spectroscopy).

Ethylene polymerization

A stainless steel autoclave reactor was charged with hexane (400 cc), $Cp^*(C_2B_9H_{11})TaMe_2$ (10 mg) and methylalumoxane (5 ml, 1.6M). The reactor was heated to 40° C. and pressurized with 200 psig (13.6 arm) (14 bar) of ethylene. The reactor was stirred for 30 minutes and vented. This procedure produced 1.5 grams of high molecular weight polyethylene.

EXAMPLE 4

Catalysis Synthesis

Synthesis of $(C_2B_9H_{11})W=NAr(Me)(Cl)$: The starting material, $W=NAr(Me)3Cl$ (Ar$=$2,6-dimethylbenzene), was prepared by known literature methods. A mixture of $W=NAr(Me)_3Cl$ (1.8 g, 5 mmol) and $(C_2B_9H_{13})$ (0.7 g, 5 mmol) in 30 ml of toluene was heated to 65° C. under an $N_2$ atmosphere. After 48 hours, the toluene was removed under reduced pressure to yield an oily red residue. The crude product was washed with pentane and filtered over a glass frit to yield a dark red solid (Yield: 1.2 g, 53%).

Ethylene Polymerization

The catalyst solution was prepared immediately before use. A solution of 30 mg $(C_2B_9H_{11})W=NAr(Me)(Cl)(Et_2O)$ and 3.0 ml, 10% MAO in toluene solution was diluted to 10 ml with toluene. Polymerization was performed in a one liter autoclave reactor at 150–200 psi (10.2–13.6 atm) (14 bar) and 40°–50° C. with 250 ml toluene. The reactor was vented after 25 min. The yield of linear PE was 6.7 g with $Mw=1.1\times10^6$ and a polydispersity of 1.8. The catalyst activity was calculated to be 536 g PE/g W.hr.

EXAMPLE 5

Ethylene Polymerization

A catalyst solution containing $(C_2B_9H_{11})W=NAr(Me)(Cl)$ (50 mg) prepared in accordance with Example 4 and 5.0 ml 10% MAO in toluene was diluted to 15 ml with toluene. The solution was added in 2.0 or 3.0 ml increments during the initial 5 minutes of polymerization to an ethylene-saturated solution of toluene (500 ml) at 80° C. The initial pressure was 200 psi (13.6 atm) (14 bar) and was increased to 300 psi (20.4 atm) and the temperature was increased to 90° C. After allowing polymerization to occur for 25 minutes, the reactor was cooled and vented. A yield of 9.8 g polyethylene was obtained with $Mw=5.6\times10^5$ and polydispersity of 2.1.

EXAMPLE 6

Propylene Polymerization

A bulk polymerization was performed at 370 psi (25.2 atm) (26 bar) with 80 ml toluene. 3.0 ml of 10% MAO in toluene was loaded into the autoclave reactor initially to act as a scavenger followed by a solution of 28 mg $(C_2B_9H_{11})W=NAr(Me)(Cl)$ prepared in accordance with Example 4 in 1 ml toluene. A temperature of 40° C. was maintained for the duration of the reaction time totaling 40 minutes. A yield of 1.5 g of polypropylene was obtained with $Mw=2\times10^4$ and a polydispersity of 5.2.

EXAMPLE 7

Catalysis Synthesis

Preparation of $W(=NAr)_2(CH_2SiMe_3)_2$ wherein Ar is 2,6-diisopropylbenzene. $W(=NAr)2Cl_2$ was prepared by known literature methods. A solution of 0.40 g $W(=NAr)_2Cl_2$ (0.70 mmol) in 20 ml $Et_2O$ was cooled to $-35°$ C. Slowly, 0.70 ml 1.0M $Me_3SiCH_2MgCl$ in $Et_2O$ was syringed into the cooled solution and the reaction mixture was allowed to stir for 17 hours while warming to room temperature. The $Et_2O$ was removed in vacuo, the crude orange solid extracted with pentane, and the extracts filtered through Celite. After removing the pentane in vacuo, 0.25 g orange $W(=NAr)_2(CH_2SiMe_3)_2$ was obtained (Yield: 47%).

Ethylene Polymerization

Toluene (500ml) was saturated with ethylene under a pressure of 200 psi (14 bar, 13.6 atm) at 80° C. in a one liter autoclave reactor. A catalyst solution of 42 mg of $W(=NiPAr)_2(CH_2SiMe_3)_2$ and 5.0 ml 10% MAO in toluene was loaded into the reactor in two 2.5 ml increments during the first 5 minutes of polymerization. The polymerization was allowed to proceed for a total of 25 minutes. The temperature was maintained at a constant 80° C. and the pressure from 200 to 250 psi (13.6 to 17 atm) (14–17 bar).

The amount of dried polymer obtained was 10.1 g, giving a catalyst activity of 721 g PE/g W.hr.

EXAMPLE 8

Catalysis Synthesis

CpNb=N(2,6-diisopropylbenzene)Me$_2$ was prepared by the reaction of MeMgI with CpNb=N(2,6-diisopropylbenzene)Cl$_2$ in diethylether at room temperature. The dichloride was prepared by known literature methods.

Ethylene Polymerization

The catalyst solution was prepared immediately before use. A solution of 80 mg CpNb=N(2,6-diisopropylbenzene)Me$_2$ and 89 mg [PhNHMe$_2$][B(C$_6$F$_5$)$_4$] was prepared in 20ml toluene. Polymerization was performed in a one liter autoclave reactor at 150–200 psi and 40°–50° C. with 500 ml hexane. The reactor was vented after 20 min. PE (as determined by $^1$H NMR) was separated from the reaction mixture (Yield: 250 mg).

We claim:

1. A composition of matter useful as an olefin polymerization catalyst comprising a coordinatively unsaturated cationic transition metal complex having at least one reactive metal-ligand sigma bond, said cation stabilized by a low coordination number polyanionic ancillary ligand system and charge balanced with at least one compatible non-coordinating anion(s).

2. The composition of claim 1 wherein the metal is one of the Groups 5 or 6 transition metals in its highest oxidation state (d$^0$).

3. A composition of matter comprising an ion-pair represented by the following formula:

$$([\{(L_3)A(L_4)\}^{-c}M_n(X)]^{+1})_q['B^{-m}]_p$$

wherein:

M is group 5 or 6 transition metal in its highest oxidation state;

n is the group number of the metal;

L$_3$ and L$_4$ are the same or different substituted or unsubstituted anionic ancillary ligands covalently bonded to the metal;

X is a uninegative ligand selected from hydride radicals, hydrocarbyl radicals, halogen-substituted hydrocarbyl radicals, halocarbyl radicals, hydrocarbyl-substituted organometalloid radicals;

A is an optional bridging group bridging L$_3$ and L$_4$;

c is an integer representing the charge on the ancillary ligand system $\{(L_3)A(L_4)\}$;

c+2=n

'B is a compatible non-coordinating anion of charge –m;

p is the number of 'B anions;

q is the number of +1 cations; and p times m=q.

4. The composition of claim 3 wherein 1 to 3 Lewis base ligands are coordinated to the metal cation.

5. The composition of claim 3 wherein 'B, is a single anionic coordination complex comprising a plurality of lipophilic radicals covalently coordinated to and shielding a central charge-bearing metal or metalloid atom, which anion is bulky, labile and capable of stabilizing the transition metal compound.

6. The composition of claim 5 wherein 'B is represented by:

$$M[Q_1Q_2..Q_n]^{-d}$$

wherein:

M is a metal or metalloid;

Q$_1$ to Q$_n$ are, independently, hydride radicals, bridged or unbridged dialkylamido radicals, alkoxide and aryloxide radicals, hydrocarbyl and substituted hydrocarbyl radicals, halocarbyl and substituted halocarbyl radicals, and hydrocarbyl- and halocarbyl-substituted organometalloid radicals and any one, but not more than one of Q$_1$ to Q$_n$ may be a halide radical;

n is the total number of Q ligands; and d is an integer representing the total charge on the anion.

7. The composition of claim 6 wherein 'B is B(pfp)$_3$Q$_1$ wherein B is boron, Q$_1$ is in accordance with claim 6, and pfp is pentafluorophenyl.

8. The composition of claim 3 wherein L$_3$ and/or L$_4$ are represented by the formula:

$$(C_4R_xH_{4-x}BR')^{-2}$$

wherein:

B is boron;

C is carbon;

each R and R' is, independently, a hydrocarbyl radical, substituted-hydrocarbyl radical, halocarbyl radical, substituted-halocarbyl radical, hydrocarbyl-substituted organometalloid radical, halocarbyl-substituted organometalloid radical, disubstituted Group 15 radical, substituted Group 16, or halogen radical; any two adjacent R groups or adjacent R and R' groups can be joined to form a cyclic substituent; and x is 0, 1, 2, 3, or 4.

9. The composition of claim 3 wherein the ligand system $\{(L_3)A(L_4)\}$ comprises at least one polyanionic ancillary ligand.

10. The composition of claim 9 wherein the polyanionic ancillary ligand set is selected from the same or different borollide, carbollide, or imido ligands.

11. A process for preparing the composition of claim 3 comprising reacting a first component comprising:

$$(i) \{(L_3)A(L_4)\}^{-c}M_nX_2$$

wherein:

M is a Group 5 or 6 transition metal in its highest oxidation state (d$^0$);

L$_3$ and L$_4$ are bulky, ancillary anionic ligands such that the sum of their formal anionic charge is equal to c;

c+2=n;

X is independently a uninegative ligand selected from hydride radicals, hydrocarbyl radicals, halogen-substituted hydrocarbyl radicals, halocarbyl radicals, hydrocarbyl-substituted organometalloid radicals, halocarbyl-substituted organometalloid radicals;

A is an optional bridging group linking L$_3$ and L$_4$; and, n is the group number of the metal;

with (ii) a second component comprising an ion-exchange compound comprising a cation, which will irreversibly react with at least one ligand, X, contained in said Group 5 or 6 metal compound and a compatible non-coordinating anion.

12. The process of claim 11 wherein the ion-exchange compound is represented by the formula:

$$[Ct^+]_m['B^{-m}]$$

wherein

Ct$^+$ is selected from Bronsted acids, ferricinium cation, tropylium cation, Ph$_3$C$^+$, and Ag$^+$;

m is the charge on 'B; and

'B is a compatible non-coordinating anion.

13. The process of claim 12 wherein Ct$^+$ is a Bronsted acid defined by LH+ where L is a neutral Lewis base and H is a proton.

14. The process of claim 12 wherein 'B is selected from anionic boranes, polynuclear boranes, carboranes, metallacarboranes, polyoxoanions, and artioic coordination complexes.

15. The process of claim 12 wherein 'B is represented by the formula:

$$M[Q_1Q_2..Q_n]^{-d}$$

wherein:

M is a metal or metalloid;

$Q_1$ to $Q_n$ are, independently, hydride radicals, bridged or unbridged dialkylamido radicals, alkoxide and aryloxide radicals, hydrocarbyl and substituted hydrocarbyl radicals, halocarbyl and substituted halocarbyl radicals, and hydrocarbyl- and halocarbyl-substituted organometalloid radicals and any one, but not more than one of $Q_1$ to $Q_n$ may be a halide radical;

n is the total number of Q ligands; and d is an integer representing the total charge on the anion.

16. The process of claim 15 wherein 'B is B(pfp)$_3$Q$_1$ where B is boron; and pfp is perfluorophenyl.

17. The process of claim 11 wherein the ligand system $\{(L_3)A(L_4)\}$ comprises at least one polyanionic ancillary ligand selected from borollide, carbollide, or imido ligands.

18. A process for preparing the composition of claim 3 comprising the reaction of a transition metal precursor composition wherein $\{(L_3)(A)(L_4)\}^{-c}M_nX_2$ is combined with a well defined Lewis acid said Lewis acid capable of abstracting the ligand X.

19. The process of claim 18 where the Lewis acid is defined by the following formula:

$$M'(Q)_r$$

wherein:

M' is a metal or metalloid in its highest oxidation state;

r represents the number of Q ligands;

and Q is selected from the group consisting of hydride radicals, dialkyamido radicals, alkoxide and alkoxide radicals, hydrocarbyl and substituted hydrocarbyl radicals, halocarbyl and substituted halocarbyl radicals, and hydrocarbyl- and halocarbyl-substituted organometalloid radicals.

20. The process of claim 19 wherein the Lewis acid is tris(pentafluorophenyl)boron.

21. A process for preparing the compositions of claim 3 comprising reacting a first component comprising the metal complex represented by:

$$\{(L_3)A(L_4)\}^{-c}M_nX$$

wherein:

M is a Group 5 or 6 transition metal in the n−1 oxidation state (d$^1$);

n is the group number of the metal;

$L_3$ and $L_4$ are ancillary anionic ligands such that the sum of their formal anionic charge is equal to c;

c+2=n;

X is independently a uninegative ligand selected from hydride radicals, hydrocarbyl radicals, halogen-substituted hydrocarbyl radicals, halocarbyl radicals, hydrocarbyl-substituted organometalloid radicals, halocarbyl-substituted organometalloid radicals; and, A is an optional bridging group bridging $L_3$ and L4; with a second component comprising a cation capable of oxidizing M to the +n oxidation state and a compatible non-coordinating anion.

22. A composition of matter comprising:

$$\{(L_3)A(L_4)\}^{-c}M_nX_2$$

wherein:

M is group 5 or 6 transition metal in its highest oxidation state;

n is the group number of the metal;

$L_3$ and $L_4$ are the same or different substituted or unsubstituted anionic ancillary ligands covalently bonded to the metal;

X is a uninegative ligand selected from hydride radicals, hydrocarbyl radicals, halogen-substituted hydrocarbyl radicals, halocarbyl radicals, hydrocarbyl-substituted organometalloid radicals, halocarbyl-substituted organometalloid radicals, halides, alkoxides, amides or phosphides;

A is an optional bridging group bridging $L_3$ and $L_4$;

c is an integer representing the charge on the ancillary ligand system $\{(L_3)A(L_4)\}$; and alumoxane.

23. The composition of claim 22 wherein the alumoxane is methylalumoxane.

24. The composition of claim 22 wherein the ancillary ligand system $\{(L_3)A(L_4)\}$ has a weight average molecular weight of about or greater than 100 grams/mole.

25. A process of preparing the composition of claim 22 comprising reacting a first component comprising the transition metal complex represented by the formula:

$$\{(L_3)A(L_4)\}^{-c}M_nX_2$$

wherein:

M is group 5 or 6 transition metal in its highest oxidation state;

n is the group number of the metal;

$L_3$ and $L_4$ are the same or different substituted or unsubstituted anionic ancillary ligands covalently bonded to the metal;

X is a uninegative ligand selected from hydride radicals, hydrocarbyl radicals, halogen-substituted hydrocarbyl radicals, halocarbyl radicals, hydrocarbyl-substituted organometalloid radicals, halocarbyl-substituted organometalloid radicals, halides, alkoxide, amides or phosphides:

A is an optional bridging group linking $L_3$ and $L_4$; with an alumoxane.

26. The composition of claim 22 placed on a support, wherein when M is a Group 6 metal the composition comprises said A bridging group.

27. The composition of claim 26 prepolymerized.

28. The composition of claim 22 selected from the group tris(pyrazolyl)borato vanadium oxide dichloride, cyclopentadienylvanadium(p-tolyimido)dichloride, Cp*(C$_2$B$_9$H$_{11}$)TaMe$_2$, wherein Cp* is C$_5$Me$_5$, (C$_2$B$_9$H$_{11}$)W=NAr$^1$(Me)(Cl), wherein Ar$^1$ is 2,6-dimethylbenzene, W(=NAr$^2$)$_2$(CH$_2$SiMe$_3$)$_2$, wherein Ar$^2$ is 2,6-diisopropylbenzene, or, CpNb=N( 2,6-diisopropylbenzene)Me$_2$.

29. The composition of claim 1 or 3 placed on a support.

30. The composition of claim 29 prepolymerized.

* * * * *